(12) United States Patent
Fiala

(10) Patent No.: US 7,287,852 B2
(45) Date of Patent: Oct. 30, 2007

(54) INTRA-OCULAR LENS OR CONTACT LENS EXHIBITING LARGE DEPTH OF FOCUS

(76) Inventor: Werner J. Fiala, Staudgasse 88/11, A-1180 Vienna (AT)

(*) Notice: Subject to any disclaimer, the term of this patent is extended or adjusted under 35 U.S.C. 154(b) by 120 days.

(21) Appl. No.: 10/562,943

(22) PCT Filed: Jun. 29, 2004

(86) PCT No.: PCT/IB2004/002182

§ 371 (c)(1),
(2), (4) Date: Dec. 29, 2005

(87) PCT Pub. No.: WO2005/001553

PCT Pub. Date: Jan. 6, 2005

(65) Prior Publication Data

US 2006/0176572 A1 Aug. 10, 2006

(51) Int. Cl.
G02C 7/04 (2006.01)
A61F 2/14 (2006.01)
A61F 2/16 (2006.01)

(52) U.S. Cl. .................. 351/160 R; 351/160 H; 623/5.11; 623/6.23

(58) Field of Classification Search ............ 351/160 R, 351/160 H, 177; 623/5.11, 6.23
See application file for complete search history.

(56) References Cited

U.S. PATENT DOCUMENTS

| 4,210,391 A | 7/1980 | Cohen |
|---|---|---|
| 4,338,005 A | 7/1982 | Cohen |
| 4,340,283 A | 7/1982 | Cohen |
| 4,637,697 A | 1/1987 | Freeman |
| 4,641,934 A | 2/1987 | Freeman |
| 4,642,112 A | 2/1987 | Freeman |
| 4,655,565 A | 4/1987 | Freeman |
| 4,775,229 A | 10/1988 | Ichihara et al. |
| 4,786,160 A | 11/1988 | Fürter |
| 4,787,722 A | 11/1988 | Claytor |
| 4,804,249 A | 2/1989 | Reynolds et al. |
| 4,828,558 A | 5/1989 | Kelman |
| 4,830,481 A | 5/1989 | Futhey et al. |
| 4,881,804 A | 11/1989 | Cohen |
| 4,898,461 A | 2/1990 | Portney |

(Continued)

FOREIGN PATENT DOCUMENTS

CA 1318799 8/1993

(Continued)

OTHER PUBLICATIONS

Encyclopaedic Dictionary of Physics, Pergamon Press, 1961, pp. 266-267.

(Continued)

*Primary Examiner*—Scott J. Sugarman
(74) *Attorney, Agent, or Firm*—Hoffmann & Baron, LLP

(57) ABSTRACT

Circular and annular lens zones are disclosed which, at a given lens area, exhibit a depth of focus of a lens of considerably smaller area. The large depth of focus is achieved by imparting the lens zones a refractive power profile. An assembly of such large depth of focus lens zones represents a lens of large diameter which lens, in polychromatic light, exhibits essentially the same depth of focus as the lens zones from which it is composed.

25 Claims, 17 Drawing Sheets cross section of a depth of focus lens (schematic)

U.S. PATENT DOCUMENTS

| | | |
|---|---|---|
| 4,936,666 A | 6/1990 | Futhey |
| 4,995,714 A | 2/1991 | Cohen |
| 4,995,715 A | 2/1991 | Cohen |
| 5,054,905 A | 10/1991 | Cohen |
| 5,056,908 A | 10/1991 | Cohen |
| 5,104,212 A | 4/1992 | Taboury et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,152,788 A | 10/1992 | Isaacson et al. |
| 5,225,858 A | 7/1993 | Portney |
| 5,229,797 A | 7/1993 | Futhey et al. |
| 5,629,800 A | 5/1997 | Hamblen |
| 5,719,704 A | 2/1998 | Shiraishi et al. |
| 5,760,871 A | 6/1998 | Kosoburd et al. |
| 5,982,543 A | 11/1999 | Fiala |
| 6,120,148 A | 9/2000 | Fiala et al. |
| 6,126,286 A | 10/2000 | Portney |
| 6,511,178 B1 | 1/2003 | Roffman et al. |
| 6,536,899 B1 | 3/2003 | Fiala |
| 6,923,539 B2 * | 8/2005 | Simpson et al. ........ 351/160 R |
| 2006/0116763 A1 * | 6/2006 | Simpson .................... 623/6.23 |

FOREIGN PATENT DOCUMENTS

| | | |
|---|---|---|
| DE | 41 30 092 | 3/1991 |
| DE | 41 34518 A1 | 4/1993 |
| EP | 0 354 786 A2 | 2/1990 |
| EP | 0 367 878 A1 | 5/1990 |
| EP | 0 375 152 A2 | 6/1990 |
| EP | 0 468 410 A1 | 1/1992 |
| EP | 0 470 811 A2 | 2/1992 |
| EP | 0 605 841 A1 | 7/1994 |
| EP | 0 741 314 A2 | 11/1996 |
| EP | 0 766 951 A1 | 4/1997 |
| GB | 1154360 | 6/1969 |
| JP | 57-161721 | 5/1982 |
| JP | 62-85229 | 4/1987 |
| WO | WO95/25288 | 9/1995 |

OTHER PUBLICATIONS

H. Haumann/G. Schröder, Bauelemente der Optik, Carl Hanser Verlag, pp. 150-151; and.

Meyers Lexikon der Technik und der exakten Naturwissen-schaften, Bibliographisches Institut, p. 1041.

* cited by examiner

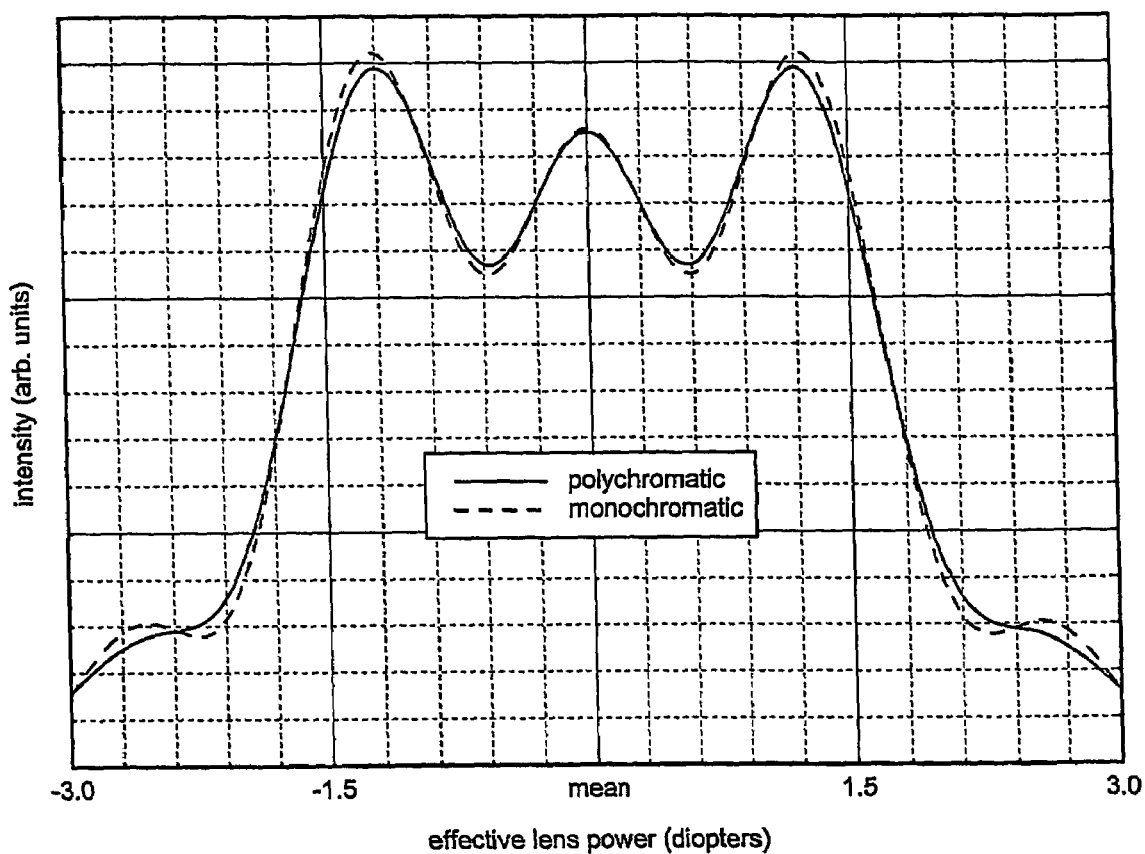
Fig 1: TFR of a circular lens of 2 mm diameter exhibiting power profile P1 of Fig. 2
monochromatic: 550 nm
polychromatic: mean wavelength = 550 nm, Gaussian distr., C.L. = 3.1 microns

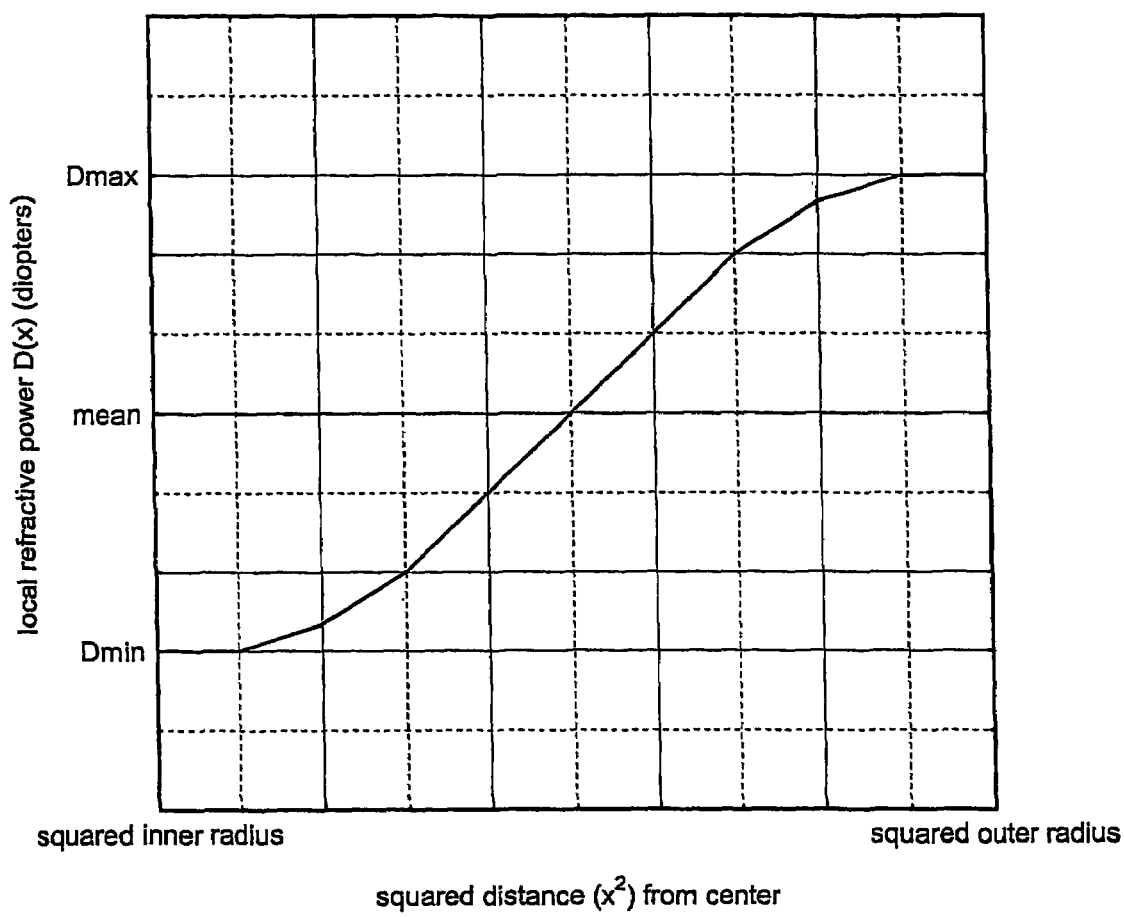
Fig 2: power profile P1 of a circular lens of 2 mm diameter or an annular lens of 3.1416 mm² area

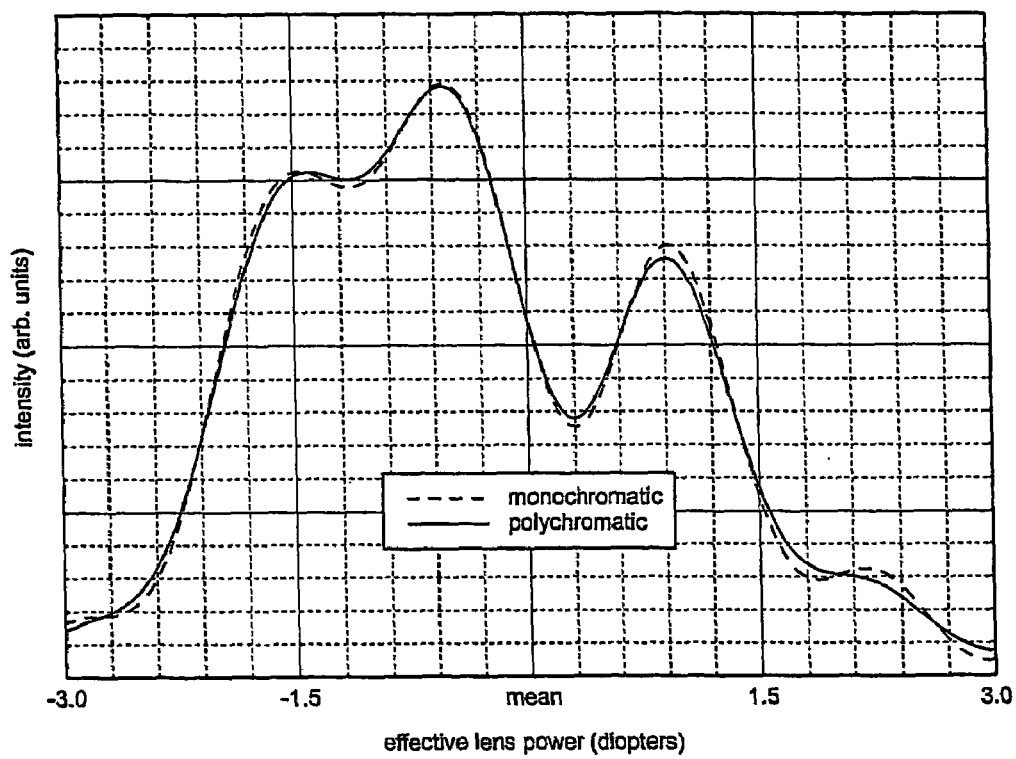
Fig 3: TFR of a circular lens of 2 mm diameter (lens zone of 3.14 mm$^2$) exhibiting power profile P2
monochromatic: 550 nm
polychromatic: 550nm mean, Gaussian distr., C.L. = 3.1 microns

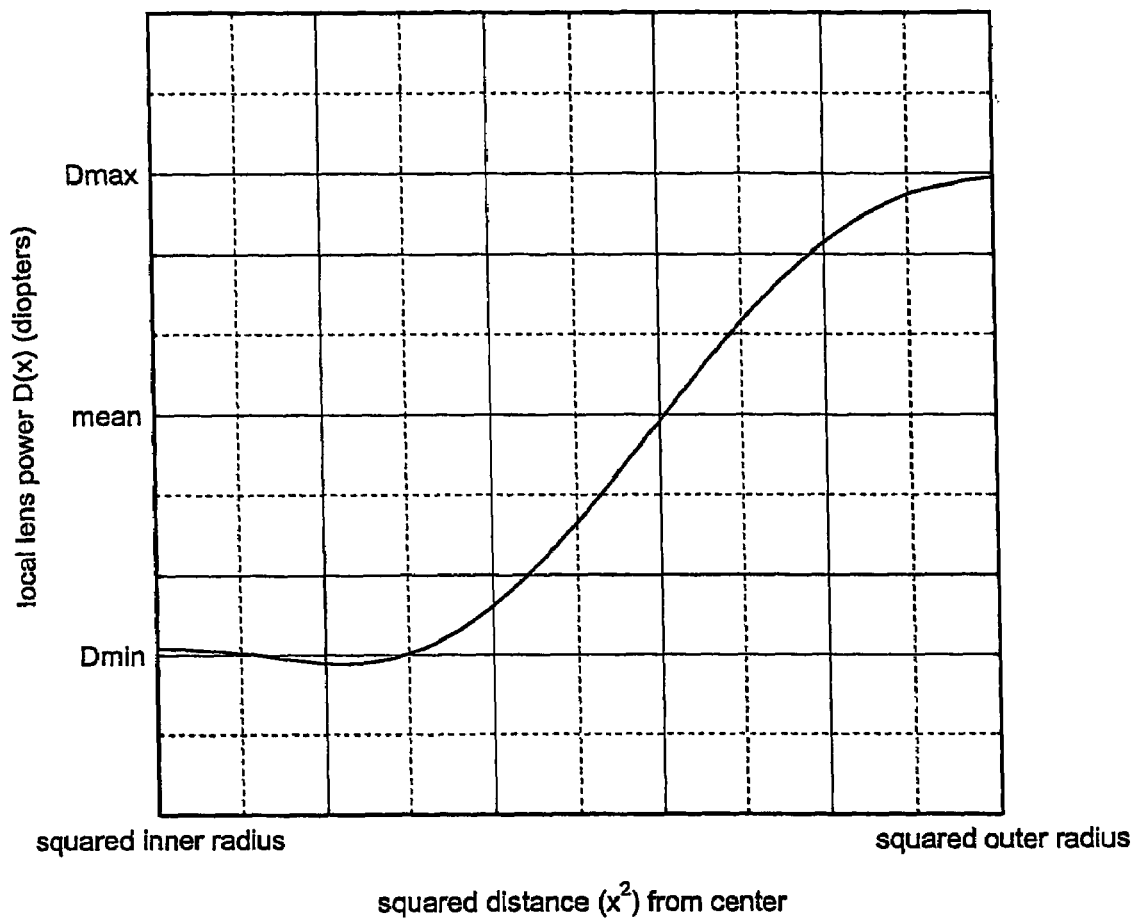
Fig 4: power profile P2 of a circular lens of 2 mm diameter or a lens zone of 3.1416 mm$^2$ area

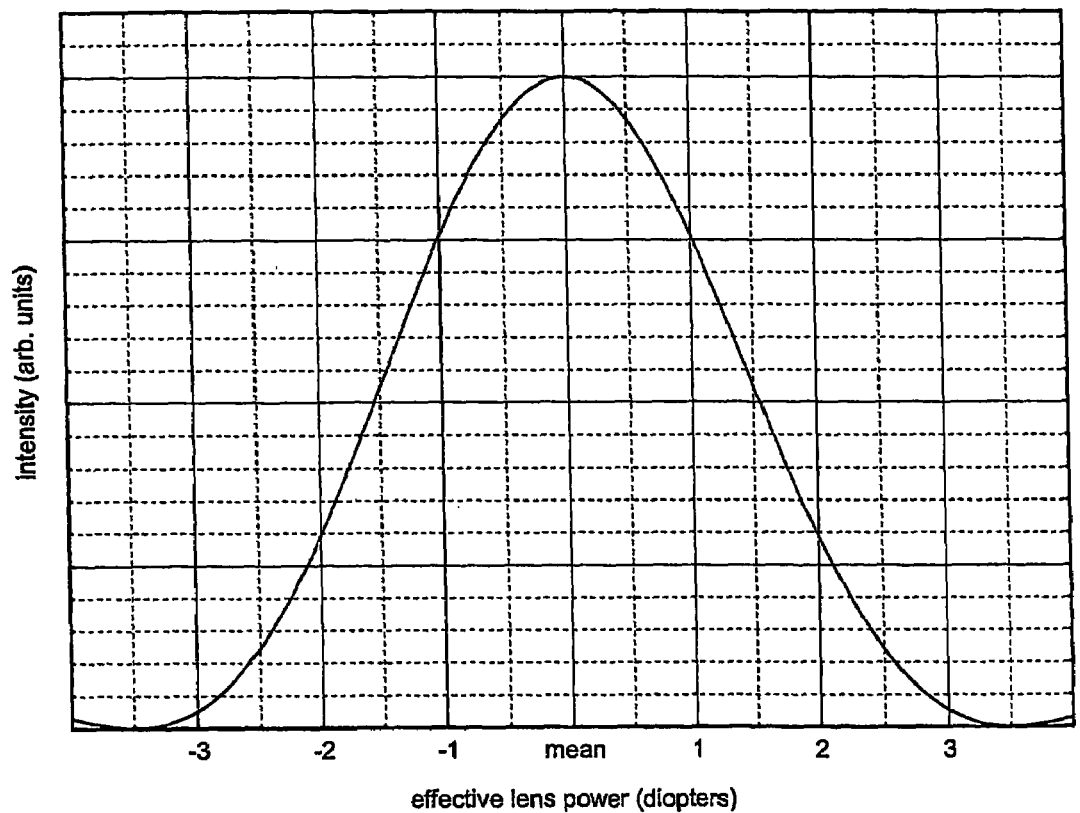
Fig 5: TFR of a lens of 1.12122 mm diameter or an annular lens zone of 1.154 mm² area
case: constant single power within lens or lens zone
constant single power = mean effective lens power
(PRIOR ART)

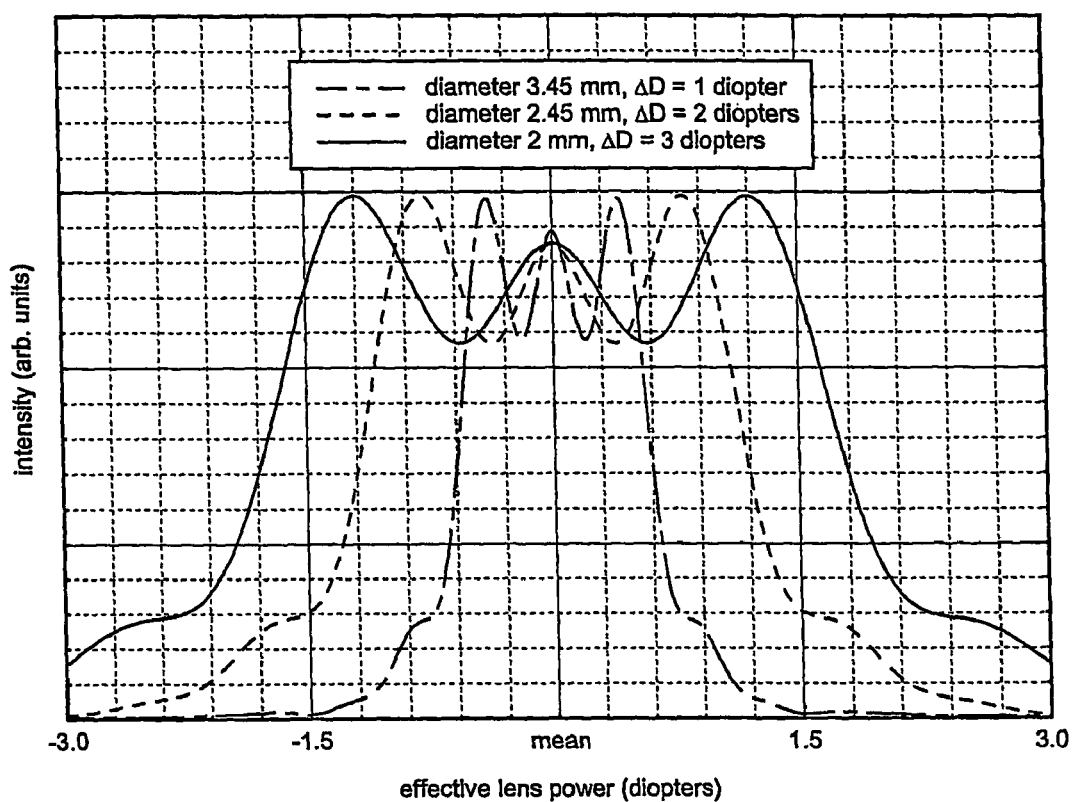
Fig 6: TFR of lenses of various diameters and power profiles
ΔD is the difference between the maxium and minimum power of the power profile of Fig. 2

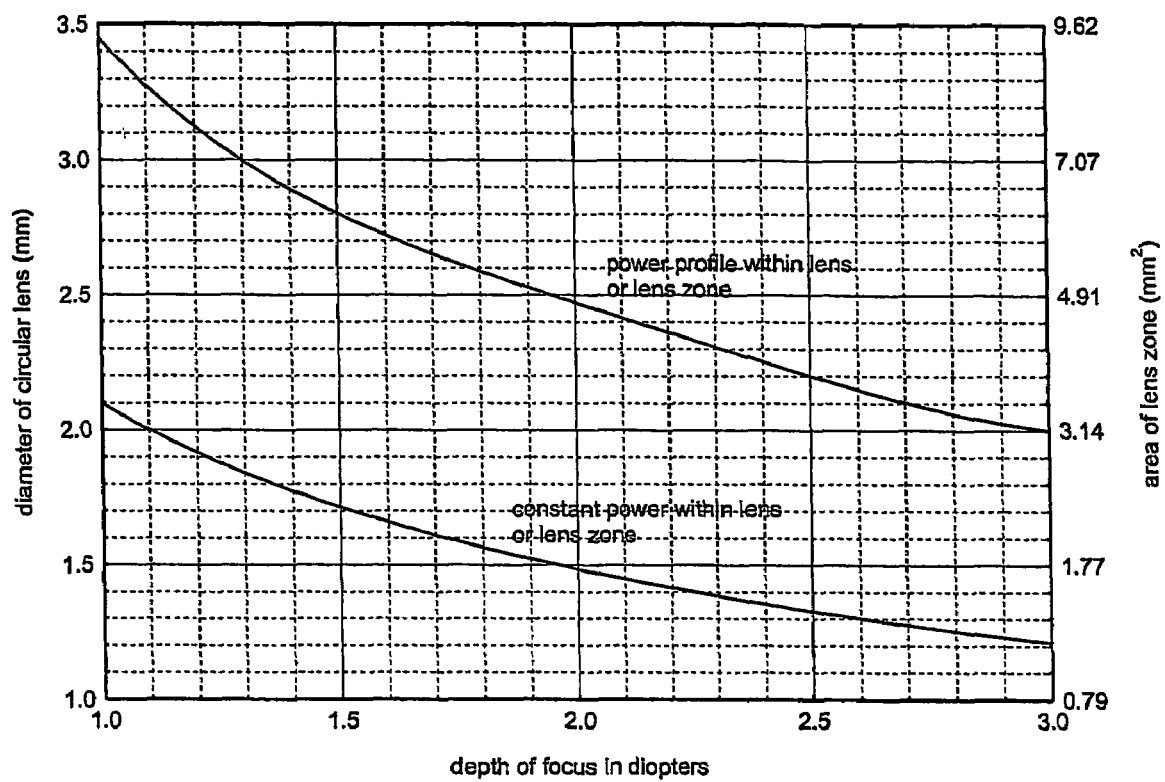
Fig 7: depth of focus vs. circular lens diameter or area of lens zone

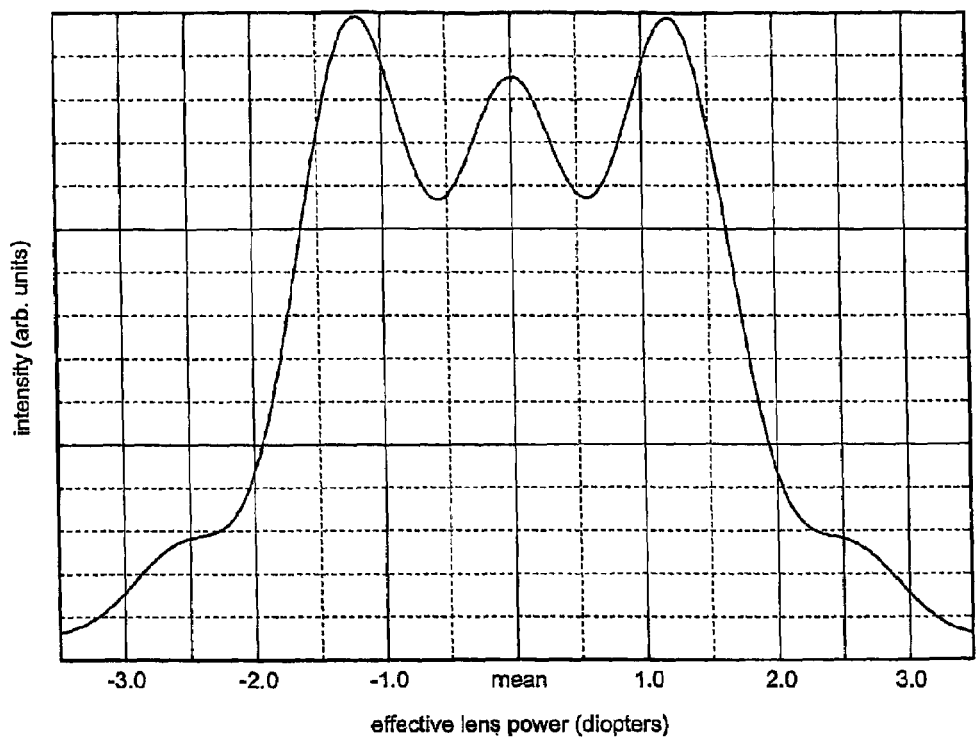
Fig 8: TFR of a depth of focus lens of 4 mm diameter in polychromatic light (coh. length = 3.1 micro lens consists of four Fresnelian zones - power profile P1 within every zone (Fig 2)

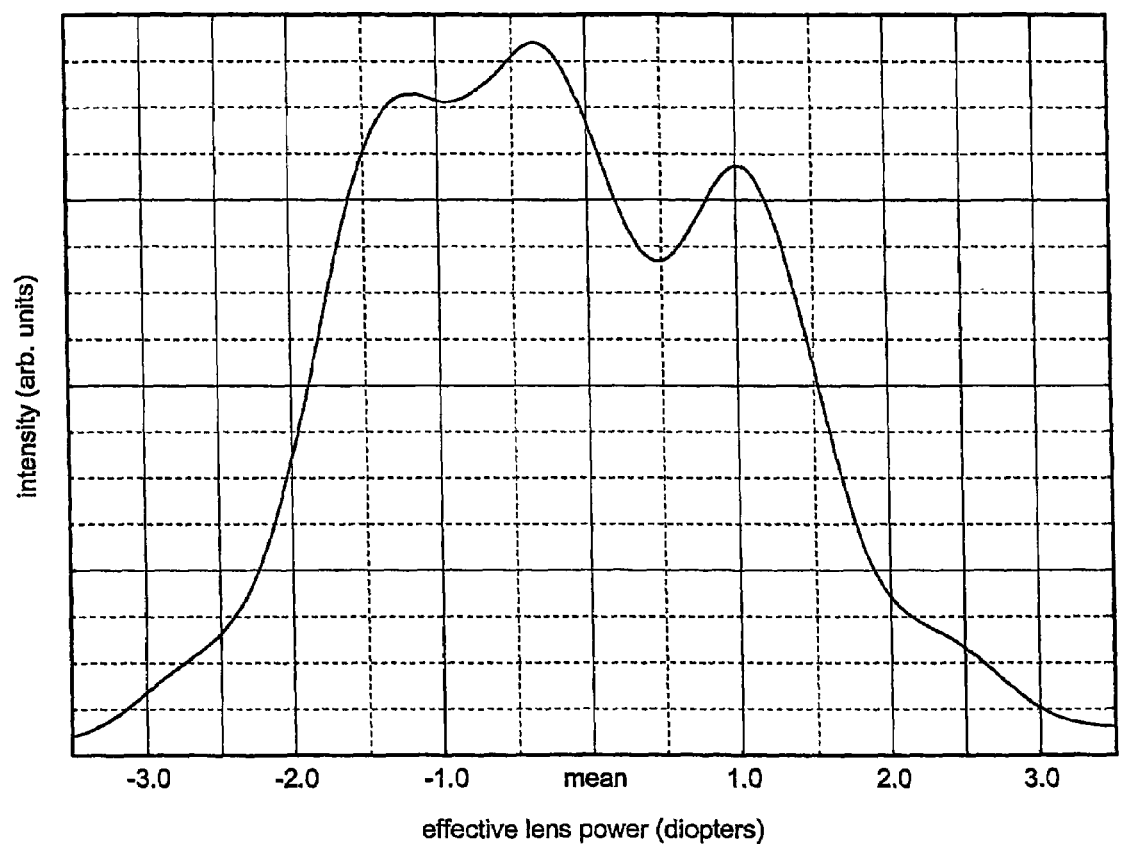
Fig 9: TFR of a depth of focus lens of 4 mm diameter comprising 4 Fresnel zones
power profile of zones 1 and 3: P1 (Fig 2)
power profile of zones 2 and 4: P2 (Fig 4)

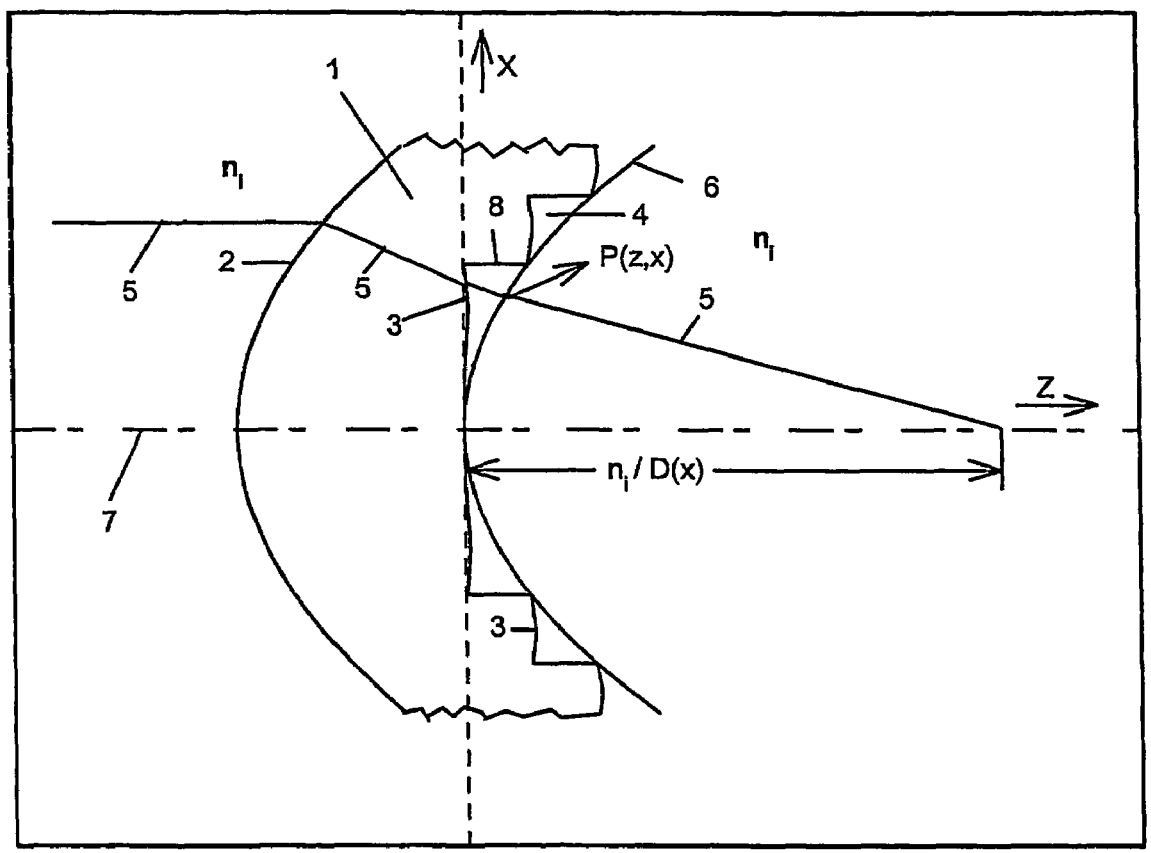
Fig. 10: cross section of a depth of focus lens (schematic)

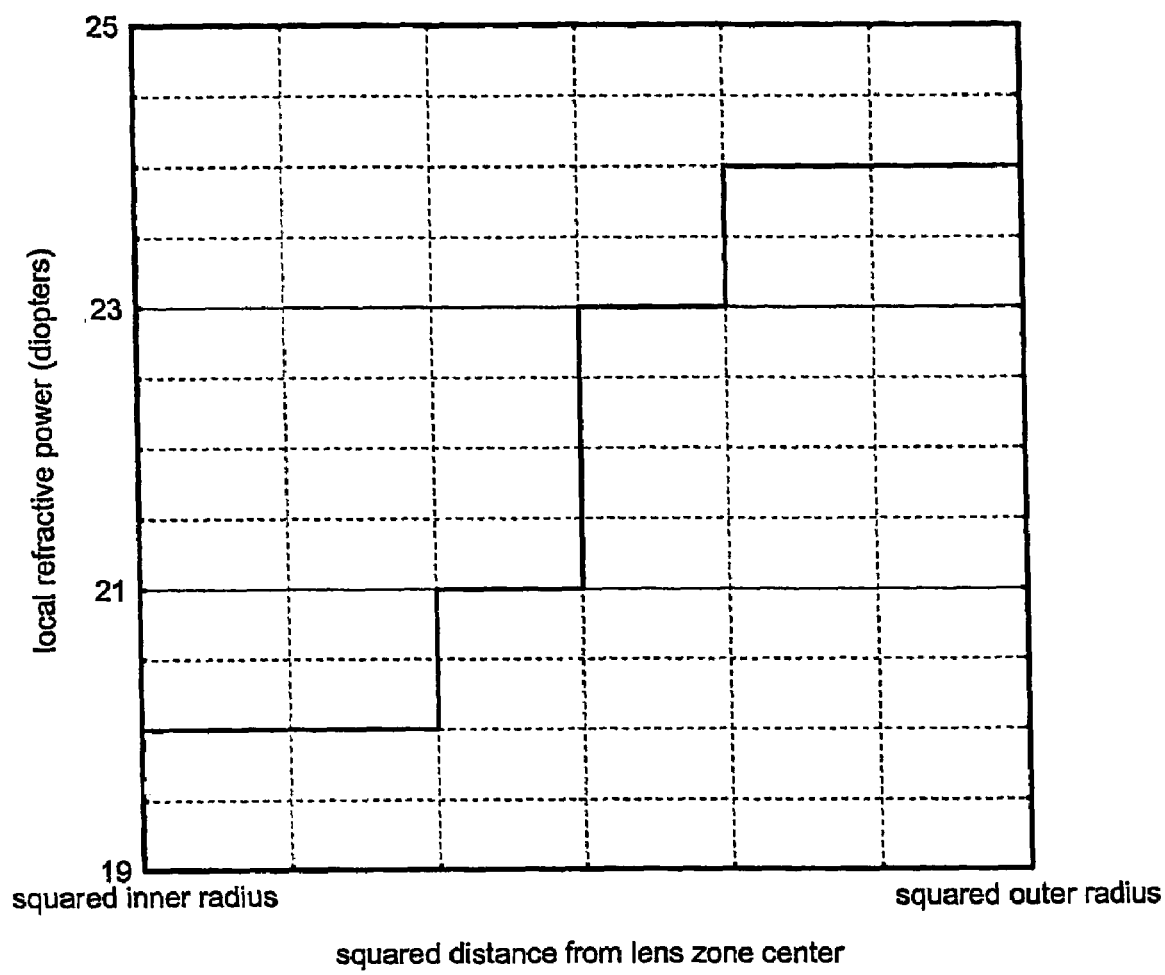
Fig. 11: approximation of power profile P1 according to figure 2

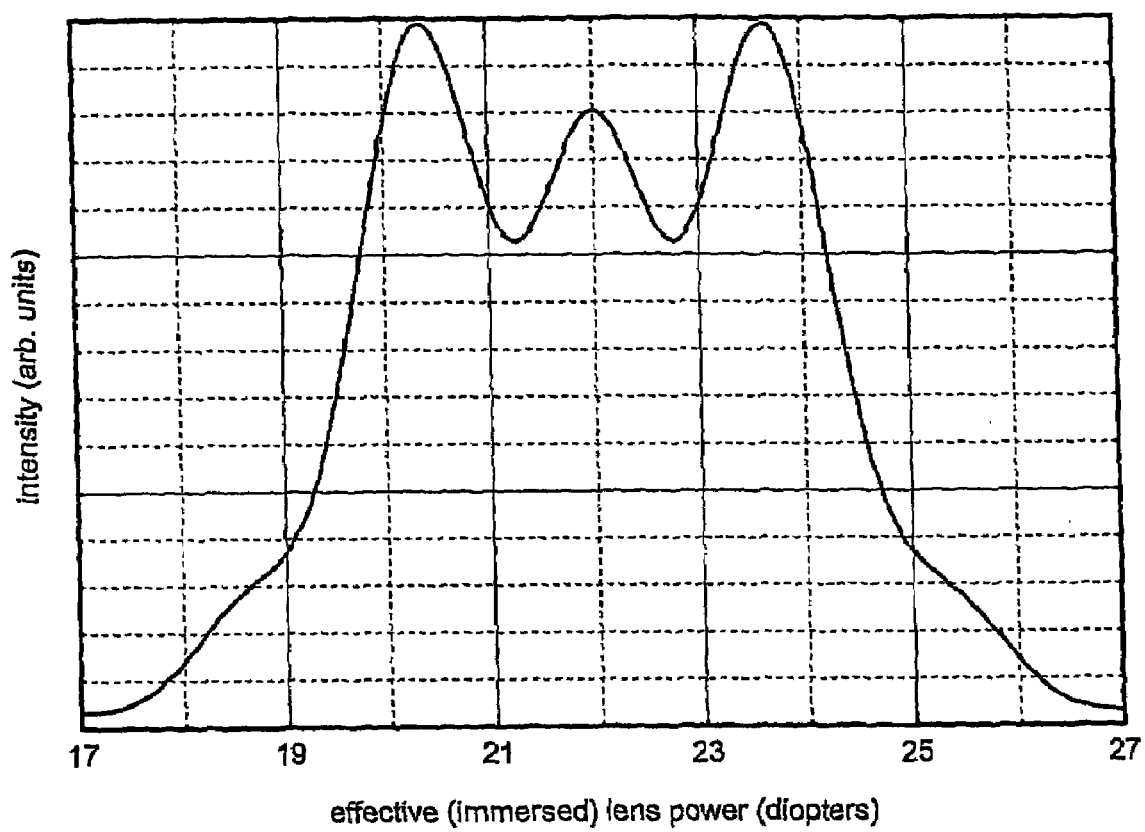
Fig. 12: TFR of an intra-ocular lens for polychromatic light of mean wavelength 550 nm and C.L. of 2.3 microns power profile of lens according to Fig. 11

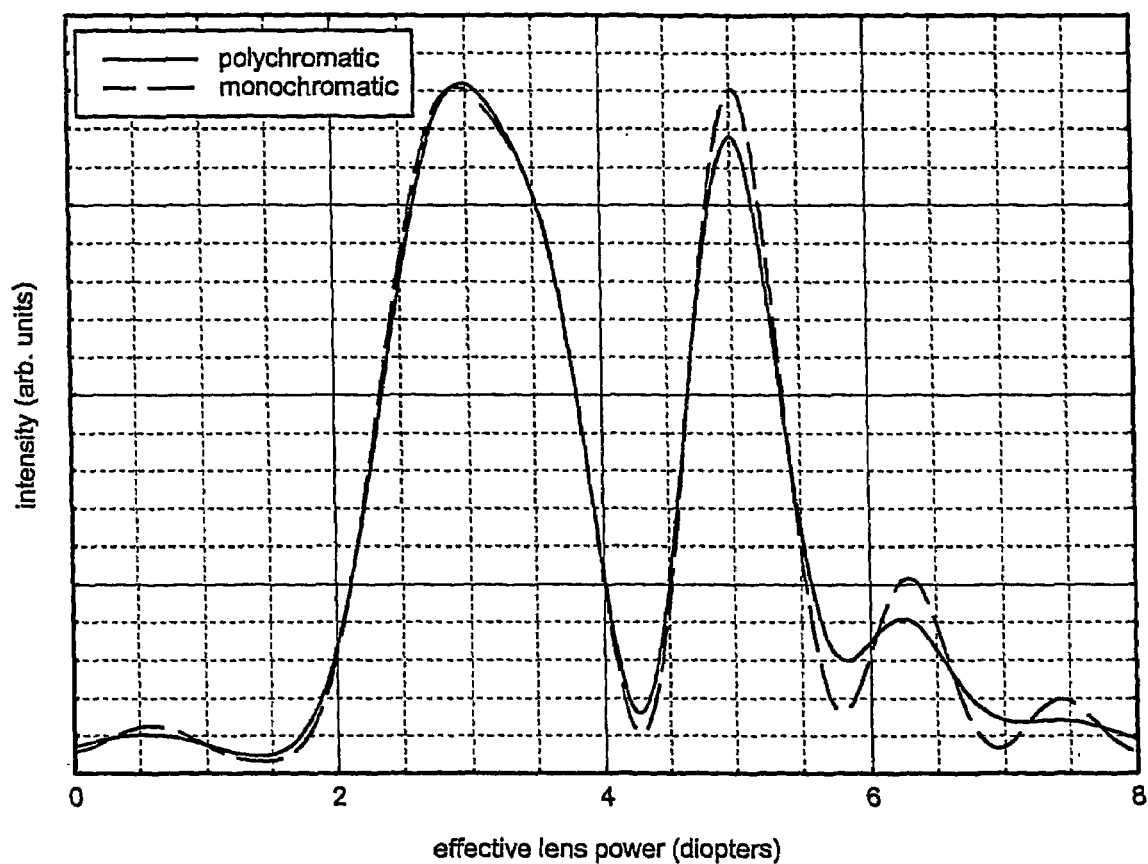
Fig. 13 A: TFR of a lens zone of 3.46 mm² area, lens zone exhibits power profile shown in Fig. 14
monochromatic light: 550 nm
polychromatic light: mean 550 nm, C.L. = 2.3 microns

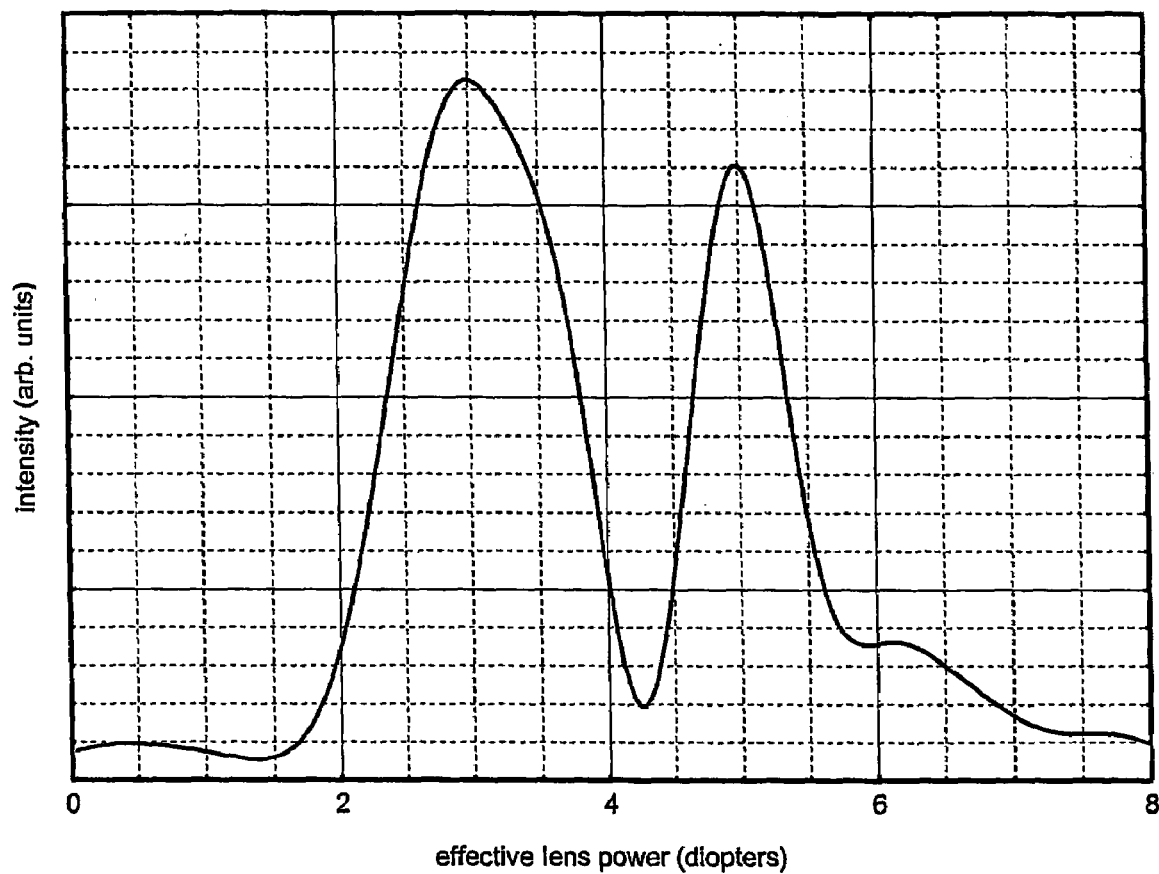
Fig. 13B: TFR of a lens consisting of 9 Fresnel lens zones on a 6.293 mm diameter polychromatic light of mean wavelength 550 nm and C.L. = 2.3 microns
lens zones have power profile according to Fig. 14

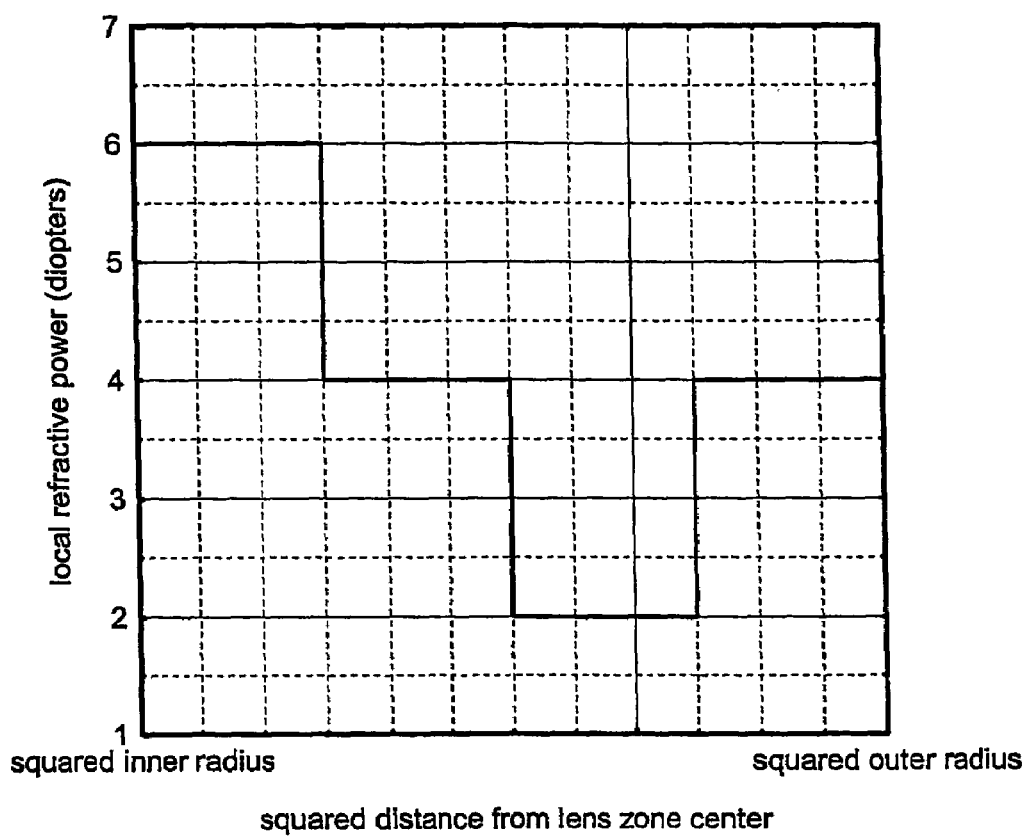
Fig. 14: refractive power profile of lens zones of lens according to figure 13

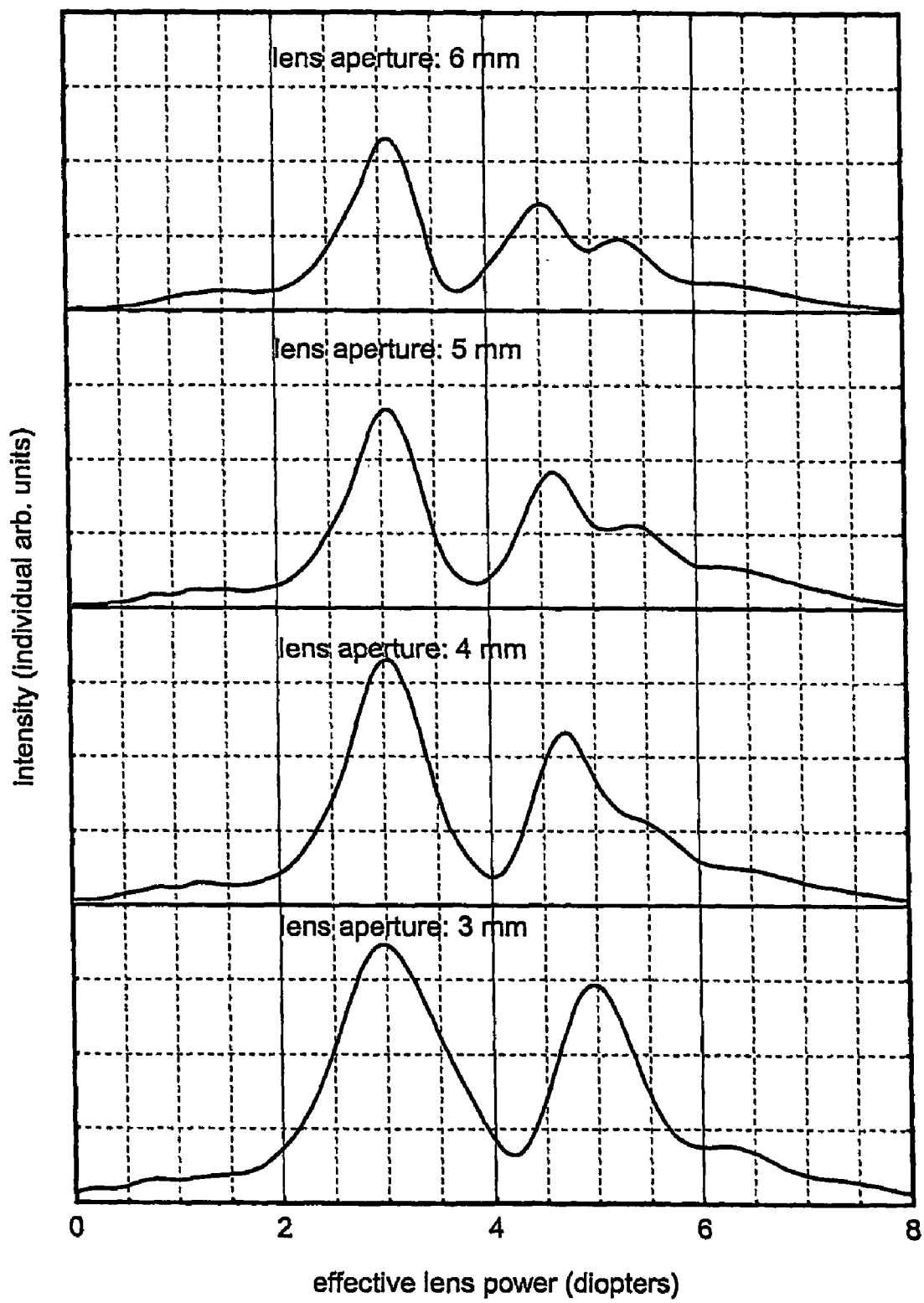
Fig. 15: TFRs for various apertures of a depth of focus lens lens zone areas increase from center to rim power profile of every zone is given by Fig. 14

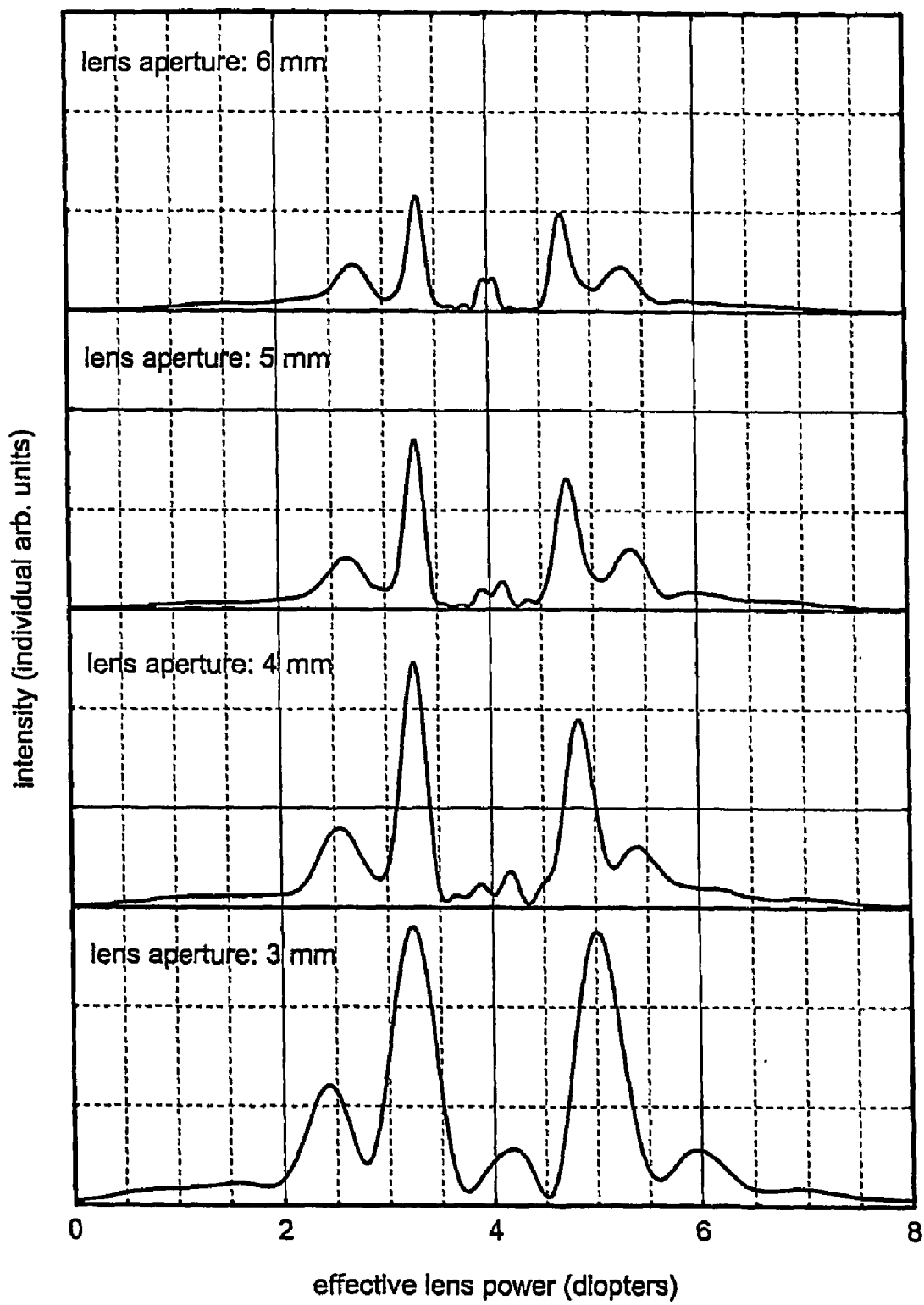
Fig. 16: TFR for various apertures of a lens consisting of lens zones like lens according to Fig. 15 but without steps between lens zones

INTRA-OCULAR LENS OR CONTACT LENS EXHIBITING LARGE DEPTH OF FOCUS

BACKGROUND OF THE INVENTION

1. Field of Invention

The invention relates to a lens and particularly to a lens which exhibits a large depth of focus.

2. Description of the Prior Art

Lenses with two or more simultaneous foci or powers are known. Such lenses, in particular in the form of contact or intra-ocular lenses, are used to correct presbyopia. The drawback of such lenses is that imaging is provided in distinct powers or foci, i.e. a "correct" image produced by the "correct" power is accompanied by a "wrong" image provided simultaneously by a "wrong" power. As a consequence, the lens user frequently experiences ghosting and halos with such lenses.

It is known that a lens of very small diameter exhibits a large depth of focus. This fact can be explained by wave optics considerations and is called the "stenopeic effect". As an example, a "pinhole lens" of 1.3 mm diameter exhibits a usable depth of focus of about 2.5 diopters. This means that objects can be seen clearly even if they are out of focus by +/−1.25 diopters from the refractive focus of this pinhole lens. Such a pinhole lens is therefore suitable to correct, or, more appropriately, "mask" presbyopia, since such a pinhole lens produces a clear image of objects the distance of which is between infinity (distance vision) and about 40 cm (near vision) in front of this lens, or, if the lens is used as a contact lens, in front of the eye.

It is further known, that such a pinhole lens also masks astigmatism within its available depth of focus. It is actually part of the diagnostic practice in the identification and quantification of the amount of astigmatism present in a human eye.

It should be noted that imaging with a pinhole lens of large depth of focus is absolutely free of ghosting, since imaging is not provided in two or more distinct foci or powers. However, the drawback of such pinhole lenses is reduced throughput of light intensity. As a consequence, imaging of distant and near objects is not satisfactory in dim light conditions.

This drawback can be eliminated with "zoned lenses" formed according to my U.S. Pat. No. 5,982,543 (W. Fiala), the disclosure of which is incorporated by reference herein. It is shown there that an annular lens of small total area exhibits a large depth of focus as well. It is further shown there that an assembly of such annular lenses or annular lens zones provides the same depth of focus like the individual zones, if measures are taken such that the individual contributions of the individual zones add incoherently. An analytical treatment of such lenses can be found in: "W. Fiala et al: Numerical Calculation of a Giant Pinhole Lens in Polychromatic Light"; Annual Report 1996, page 39, editor: Physikalisches Institut, Universitaet Erlangen-Nuernberg", the disclosure of which is incorporated by reference herein.

In a lens according to U.S. Pat. No. 5,982,543 a rather large number of annular zones is required in order to provide a sizeable depth of focus. In such a lens design, a depth of focus of at least one diopter requires lens zones the maximum area of which is limited to a value $F=0.0056 \lambda mm^2$, F being the maximum area of any of the lens zones, and $\lambda$ the average wavelength in nanometers. Assuming the common value $\lambda=550$ nm, the maximum zone area is calculated to be 3.08 mm$^2$.

In order to achieve a depth of focus of 2.5 diopters with a lens made according to my U.S. Pat. No. 5.892,543, the area of the individual lens zones exhibits a value of approximately 1.33 mm$^2$; this means that a lens of 6 mm diameter would have to comprise twenty-one (21) such zones. Although the production of such a lens is possible, in principle, the production requirements are high.

OBJECTS AND SUMMARY OF THE INVENTION

It is an object of the present invention to provide a lens of sizeable diameter which lens exhibits a large depth of focus and comprises fewer zones than a lens formed in accordance with my U.S. Pat. No. 5,982,543.

It is a further object of the present invention to provide a lens or annular lens of given area which exhibits a larger depth of focus than a lens or annular lens of constant lens power and same area.

It is a further object of this invention to provide a lens with an increased depth of focus, wherein the intensities of the powers within the depth of focus are approximately constant.

It is a further object of the present invention to provide a lens with increased depth of focus, wherein the intensities of the powers within the depth of focus can be given desired values.

It is another object of the present invention to provide a lens with large depth of focus which lens is employed in the correction of presbyopia.

It is another object of the present invention to provide a lens with large depth of focus which lens is employed in the correction of corneal astigmatism.

It is yet another object of the present invention to provide a lens of large depth of focus which lens is employed in the correction of irregular astigmatism.

It is still another object of the present invention to provide a lens with large depth of focus which lens is employed in the correction of regular or irregular astigmatism and which correction is independent of the angular position of the lens.

It is another object of the invention to provide a large diameter lens with increased depth of focus which is easy to manufacture.

Other objects of this invention will become apparent in the course of the following discussion.

As will be shown in the following, the above-mentioned objects are achieved by imparting a lens or an annular lens a suitable refractive power profile instead of a single refractive power. Such a lens or lens zone then exhibits a depth of focus which is substantially larger than a lens or lens zone of single given power and of the same area. The power profile imparted to the lens or lens zone is available for design purposes, i.e. different such power profiles result in different intensity distributions within the depth of focus of the lens or annular lens. Using appropriate power profiles, it is therefore possible to attribute different relative intensities to different powers within the available depth of focus of the lens or annular lens. A lens of sizeable diameter and large depth of focus is provided by an assembly of such lens zones, and measures are taken in order to achieve incoherent summation of the contributions of the individual lens zones.

Specifically, the invention includes a lens zone exhibiting a depth of focus such that the lens zone includes a refractive power profile. The power profile is configured such that the depth of focus is at least 1.1 diopters for light of 550 nm wavelength, and wherein the area of the lens zone is at least 3.14 mm$^2$. Preferably, the refractive power profile is more specifically configured such that the intensities within the depth of focus are at least 50% (fifty percent) of the peak intensity within the depth of focus. Furthermore, the refractive power profile may be configured such that the lens zone is a multifocal lens zone with at least two powers such that at least one of the powers exhibits the depth of focus. It may also be considered that the power profile of the lens zone represents an approximation of a combination of at least one constant function and a fraction of a period of a sinusoidal function.

The present invention may include a lens exhibiting a large depth of focus which is formed from at least two lens zones. Each lens zone has a refractive power profile wherein the depth of focus is at least 1.1 diopters for light of 550 mm wavelength and the area of each of said lens zones is at least 3.14 mm$^2$. The lens is further configured such that optical path length differences are provided between adjacent lens zones such that light rays passing through adjacent lens zones have an optical path length between an object point and an image point which are different by at least a coherence length of the light used, which is at least 1 μm. The lens of the present invention may include lens zones such that the refractive power profiles of the lens zones are identical. Alternatively, the refractive power profiles of the lens zones may be formed to be different. The lens may also be provided to be a multifocal lens whereby each of the lens zones exhibits a refractive power profile having at least two powers and wherein at least one of the powers exhibits the depth of focus. The lens may be formed such that the areas of all lens zones are equal. Alternatively, the lens may be configured such that the areas of all lens zones are different. The lens is suitable to be an ophthalmic lens, a contact lens, an intra-ocular lens, or an intra-corneal lens.

The lens of the present invention exhibits a large depth of focus by providing at least two lens zones which include a central circular lens zone and at least one annular lens zone surrounding the circular lens zone. Each of the lens zones is configured such that light rays passing through adjacent lens zones have an optical path length difference between an object point and an image point which are different by at least a coherence length of light passing through which is at least 1 μm. The area of any of the lens zones is at least 3.14 mm$^2$. The lens zones are given refractive power profiles such that the depth of focus of any of the lens zones is at least 1.1 diopters for light of 550 nm wavelength. The lens may be formed such that the shape of the through focus response of any of the lens zones is substantially identical with the shape of the through focus response of the entire lens. The lens may be used as an ophthalmic lens, a contact lens, an intra-ocular lens or an intra-corneal lens.

BRIEF DESCRIPTION OF THE DRAWINGS

FIG. 1 illustrates the through focus response (TFR) of a lens according to the present invention.

FIG. 2 illustrates the refractive power profile ("P1") imparted to the circular lens with TFR according to FIG. 1, wherein $\Delta D=D_{max}-D_{min}=3$ diopters.

FIG. 3 illustrates the TFR of another circular lens or annular lens according to the present invention such that higher effective lens powers are weighted less than lower effective lens powers.

FIG. 4 illustrates a further refractive power profile ("P2") imparted to a circular lens or annular lens with TFR according to FIG. 3, wherein $\Delta D=D_{max}-D_{min}=3$ diopters.

FIG. 5 (prior art) illustrates the TFR of a prior art lens of 1.2122 mm diameter (area: 1.154 mm$^2$) such that the depth of focus of this prior art lens is essentially equal with the depth of focus of the lenses according to FIG. 1 and FIG. 3.

FIG. 6 illustrates various TFRs of circular lenses (or annular lenses with the same area as the circular lenses), wherein all circular lenses (or annular lenses) are imparted a power profile according to FIG. 2.

FIG. 7 illustrates the required diameter of a circular lens and the required area of a lens zone as a function of the desired depth of focus for a lens zone with constant refractive power and for a lens zone with a power profile P1 or P2.

FIG. 8 illustrates the TFR of a depth of focus lens of 4 mm diameter consisting of four zones of equal area (Fresnel zones, area: 3.14 mm$^2$ each) in polychromafic light, wherein all zones exhibit the same power profile P1.

FIG. 9 illustrates another TFR of a depth of focus lens of 4 mm diameter consisting of 4 zones of equal area (Fresnel zones, area 3.14 mm$^2$ each) in polychromatic light, wherein zones 1 and 3 exhibit power profile P1 and zones 2 and 4 exhibit power profile P2.

FIG. 10 illustrates the cross-section of an embodiment of a depth of focus lens according to this invention.

FIG. 11 illustrates another refractive power profile imparted to lens zones according to this invention, wherein the refractive power profile is discontinuous and consists of four (4) discrete refractive powers within the lens zone.

FIG. 12 illustrates the TFR of a large depth of focus lens which consists of lens zones, each of which is imparted the power profile shown in FIG. 11.

FIG. 13A illustrates the TFR of yet another lens with large depth of focus, wherein the lens exhibits increased depth of focus in two distinct powers and the lens zones exhibit a power profile as shown in FIG. 14.

FIG. 13B illustrates the TFR of lens having nine (9) Fresnel Zones on a lens of 6.293 mm diameter, each zone having a power profile as shown in FIG. 14.

FIG. 14 illustrates the discontinuous power profile of the lens zones of the large depth of focus lens such that the TFR of which is shown in FIG. 13A and the TFR of the large depth of focus lens is shown in FIG. 13B.

FIG. 15 illustrates various TFRs of yet another lens with large depth of focus according to this invention, wherein the TFRs are dependent on lens aperture or pupil size.

FIG. 16 illustrates various TFRs of a lens including lens zones according to FIG. 15 but without steps between lens zones.

DETAILED DESCRIPTION OF PREFERRED EMBODIMENTS

For the sake of simplicity and clarity, the following terms used in this invention disclosure are defined as follows:

"annular lens": a lens which is confined to an annular ring with an inner bonding radius and an outer bonding radius.

"circular lens": a lens which is confined to a circular disk of radius r. (A circular lens is what is usually considered 'a lens').

"lens zone": a lens zone is either a circular lens or an annular lens. The circular lens can be interpreted as an annular lens with inner bonding radius 0 and outer bonding radius r.

"Fresnel zones", "Fresnel lens zones": lens zones which exhibit the same area $\pi(r_O^2-r_I^2)$, $r_O$ being the outer bonding radius and $r_I$ being the inner bonding radius of one of the lens zones.

"refractive power profile", "power profile": the function D(x) of the refractive power at a radial distance x from the center of a lens zone vs. the squared distance $x^2$. The refractive power is calculated on the basis of Snell's refraction law. Power profiles are called "P1, "P2", etc.

"through focus response (TFR)": the distribution of light intensity along the axis of a lens or lens zone when a plane wave of light is incident on the lens or lens zone in parallel with the axis of the lens or lens zone.

"effective lens power": the index behind a lens or lens zone divided by the distance (in meters) on the lens axis behind said lens or lens zone.

"depth of focus": the width in diopters of the TFR at a minimum of 40.5 % of the peak intensity of the TFR, respectively.

"coherence length": the value $\lambda^2/\Delta\lambda$ of a polychromatic light spectrum, $\lambda$ being the mean wavelength, and $\Delta\lambda$ being the half-width of the wavelength distribution. The abbreviation "C.L." is used in this disclosure. The C.L. of white light is 1 micron ($\lambda$=550 nm, $\Delta\lambda$=300 nm).

The refractive power or power profile of a circular lens or annular lens determines the resultant wave front of light into which an incident, e.g. plane, wave is converted by this circular or annular lens. This wave front determines the resulting intensity distribution along the axis of the circular lens or annular lens, i.e. it determines the through focus response (TFR). The calculation of the TFR as a result of the refractive power profile of a circular or annular lens zone can be done analytically; one such method for this calculation is presented in: W. Fiala and J. Pingitzer: Analytical Approach to Diffractive Multifocal Lenses, Eur. Phys. J. AP 9, 227-234 (2000), the disclosure of which is incorporated by reference herein. The algorithm presented in this publication is used for the present calculations of the TFR of lenses and of assemblies of lens zones with optical steps between the individual lens zones.

FIG. 1 illustrates the TFR of a circular lens of 2 mm diameter exhibiting a power profile P1 as shown in FIG. 2. For purposes of FIG. 1, we assume a monochromatic light wavelength of 550 rum and a polychromatic mean wavelength of 550 nm and further a Gaussian wavelength distribution which results in a C.L of 3.1 microns. The TFR of FIG. 1 indicates that this lens zone exhibits a depth of focus in excess of 3 diopters. Particular mention is made of the fact that this lens zone exhibits an area of 3.14 mm$^2$; a lens zone with 3.14 mm$^2$ area and constant refractive power would exhibit, by comparison, a depth of focus of only 1.1 diopters. It should also be noted that the intensities within the depth of focus vary only slightly by comparison, which is an advantage. In any case, the intensities within the depth of focus are larger than 50% of the peak intensity. Also the fall-off of the intensities at the limits of the depth of focus is steep; the result of this steep fall-off is increased intensity within the usable depth of focus. Suitable refractive power profiles cannot easily be calculated back from a desired shape of the TFR, since the resulting TFR is determined by diffraction effects rather than the refraction law (Snell's law). But with modem calculation tools it is possible to select the proper refractive power profile with a lens or annular lens zone for a desired shape of the TFR Such calculations are usually done on a "trial and error" basis.

FIG. 2 illustrates a power profile P1 of a lens zone of 3.14 mm$^2$ total area. The resulting TFR of such a lens zone is illustrated in FIG. 1. Power profiles and the resulting TFR of the above-discussed type of lens zone are suitable for correction of presbyopia and astigmatism. In presbyopia correction, it is occasionally desired to attribute more light intensity to the distance power than to the near power, or vice versa FIG. 3 illustrates an example of such a desirous TFR. FIG. 3 shows the TFR of a circular lens of 2 mm diameter (lens zone of 3.14 mm$^2$) exhibiting a power profile P2 as shown in FIG. 4. Once again, we assume the same parameters regarding the light wavelengths as set forth in FIG. 1. Such a lens or lens zone provides a sizeable depth of focus and intensity in the distance power and somewhat less intensity in the near power. Since the minimum intensity within the depth of focus is more than 50% of the maximum intensity within the depth of focus, the full depth of focus is preserved within a range of over 3 diopters. As a consequence, ghosting or halos will not be present with this lens zone at all.

In FIG. 4, another suitable power profile P2 (i.e., the function D(x) versus $x^2$) of a lens zone is illustrated which provides a non-symmetric intensity distribution in the TFR. The presented power profile provides more intensity in the smaller powers of the TFR. The power profile according to FIG. 4 underlies the lens zones the TFR of which is shown in FIG. 3.

As said, the usable depths of focus of the discussed circular or annular lenses formed in accordance with FIGS. 14 was in excess of 3 diopters. The total lens area of these lens zones was 3.14 mm$^2$. For comparison, a prior art circular lens or annular lens of a given single refractive power is shown in FIG. 5. Should such a circular or annular lens exhibit also a depth of focus in excess of 3 diopters, the maximum area of this circular or annular lens has to be limited to 1.154 mm$^2$, i.e. a value almost a third smaller than the area of a circular or annular lens according to the present invention. A prior art lens zone of 3.14 mm$^2$ area would exhibit a depth of focus of only 1.1 diopters.

Should smaller values for the depth of focus be desired, the same principal shape of a given power profile can be applied on lens zones of larger area. The difference between the maximum and the minimum refractive power in the power profile has to be adjusted accordingly. FIG. 6 illustrates three examples of TFRs of essentially similar shape but having different depth of focus. The results are presented for circular lenses of varying diameter. From the above discussion, it is evident that these results would also apply for annular lenses which exhibit the same areas as the circular lenses. As can be seen from the results in FIG. 6, the difference $\Delta D$ in the power profile as well as the diameter of the circular lens (or the area of an annular lens) determine the available depth of focus. For example, a difference $\Delta D=D_{max}-D_{min}=2$ diopters results in a lens or annular lens with a depth of focus somewhat in excess of 2 diopters; this depth of focus will be in a lens of diameter 2.45 mm (area: 4.71 mm$^2$). For other lens diameters (or lens zone areas) the same difference $\Delta D$ would result in TFRs of different shapes. This is another example of the importance of diffraction phenomena associated with refractive lenses.

Thus, a circular lens or annular lens according to this invention can provide a depth of focus which is much larger than that of a circular lens or annular lens of same area and given single power. The results are summarized in FIG. 7 and apply for lens zones which exhibit power profiles according to FIG. 2 and/or 4. As can be seen from FIG. 7, much larger lens diameters or lens zone areas are possible in a circular lens or annular lens according to the present invention than in a conventional circular or annular lens of same depth of focus. By way of example, a depth of focus of 2 diopters is achieved with a circular lens or annular lens of single refractive power of 1.77 mm$^2$ area, whereas a circular lens or annular lens according to the present invention exhibits an area of approximately 4.9 mm$^2$.

An assembly of a central circular lens and surrounding annular lens zones according to the present invention represents a large aperture lens which exhibits the depth of focus of a much smaller lens. FIG. 8 illustrates the TFR of a lens of 4 mm diameter; this lens consists of four lens zones of 3.14 mm² each; every lens zone exhibits a refractive power profile like the one shown in FIG. 2, wherein $D_{max}-D_{min}=3$ diopters. The innermost lens zone is a circular lens of 2 mm diameter. Every lens zone of the lens according to this invention exhibits a depth of focus of appr. 3.5 diopters; this large depth of focus is due to the fact that every lens zone is given a refractive power profile instead of a constant refractive power. By comparison, lens zones of 3.14 mm² area and constant refractive power would exhibit a depth of focus of only 1.1 diopters.

It is also possible, to combine lens zones which exhibit different power profiles in a lens of large depth of focus and large diameter. FIG. 9 illustrates an example for the TFR of such a lens according to the present invention. The lens of 4 mm diameter consists again of four Fresnel zones of equal area. Contrary to the example according to FIG. 8, the individual lens zones do not exhibit the same refractive power profile. In the lens according to FIG. 9 the uneven lens zones exhibit the refractive power profile according to FIG. 2 (P1) and the two even lens zones feature the power profile according to FIG. 4 (P2). By combining lens zones of different power profiles it is possible to create a large aperture lens with large depth of focus wherein the intensity distribution within the depth of focus assumes a desired function. The topographical dimensioning of the annular lens zones in such a way that they exhibit a certain desired refractive power profile is state of the art and e.g. extensively discussed in WO 01/04667 A1 (W. Fiala), the disclosure of which is incorporated by reference herein.

The assemblage of annular zones such that the contributions of the individual lens zones add incoherently, i.e. in independence of one of the other, is state of the art and extensively discussed in U.S. Pat. No. 5,982,543 (W. Fiala), the disclosure of which is incorporated by reference herein. Incoherent imaging is achieved by introducing optical path length differences between adjacent annular zones in excess of the coherence length of the polychromatic light used in imaging with this lens. With these measures, the lens of large aperture exhibits the same depth of focus in polychromatic light like the individual lens zones it is made up of.

By way of example, FIG. 10 shows part of a large depth of focus contact lens 1 according to the present invention; this lens consists of lens zones which exhibit refractive power profiles, and optical path length differences are provided between adjacent lens zones. In dimensioning this lens, the position of the focus pertaining to a given value D(x) of the power profile is calculated first; this position is given by the distance $n_i/(D(x)$ from the back vertex of the lens. From this focus, a light ray 5 is directed into the point P(z,x) on the envelope 6 of the back surface of the large depth of focus lens. This light ray is then refracted at the interface 6 between the immersion medium with index $n_i$ and the tear fluid 4 with index 1.336. Then the resulting ray is refracted at the interface 3 between the tear fluid and the lens medium; the resulting light ray is then refracted at the interface 2 between the lens medium and the immersion medium. The resulting light ray after this refraction has to be parallel to the lens axis 7 (light incidence from infinity): this can be achieved by variation of the inclination of the surfaces 3 and 2 in a trial and error method. Surface 2, in general is a multi-curve; but it is also possible to design a lens with a front mono curve (e.g. a sphere).

The described procedure has to be carried out for all values of x of the power profile D(x). Usually, the procedure starts with x=0 and then the value of x is increased in accordance with the given power profile. When the value for x coincides with the outer bonding radius of the considered lens zone, a step 8 is introduced such that this step provides the required path length difference between adjacent lens zones. Step 8 is not necessarily in parallel with the lens axis 7. This path length difference is in the order of $t(n_1-n_{tr})$, wherein t is the topographical step height, $n_1$ is the lens index and $n_{tr}$ is the index of the tear fluid. The topographical step height may have to be adjusted such that the optical path length difference assumes a certain desired minimum value. Then the entire procedure as described above has to be repeated with new initial values for the (local) inclination of the front surface 2.

As will be appreciated, the entire dimensioning procedure relies on modern computation tools, since usually many trial runs are necessary in order to arrive at the lens topography which corresponds to the required power profile.

Should it be desired that the front surface is given by a mono curve (e.g. a sphere), then the steps 8 are a result of the chosen parameters which describe the front surface (e.g. front radius and center thickness). Then a minimum optical step height T has to be defined, and the relevant parameters have to be varied until all resultant steps 8 are sufficiently large such that $abs(t(n_1-n_{tr}))>T$, where T is the desired minimum optical path length difference. For the case of a contact lens, the index of the immersion medium is $n_i=1$. By comparison, the index of the immersion medium is $n_i=1.336$ for the case of an intra-ocular lens; in the case of an intra-ocular lens, the index $n_{tr}$ of the medium adjacent to the lens will also assume the value 1.336. It may also be desired that the large depth of focus lens exhibits smooth outer surfaces, e.g. in the case of an intra-corneal or contact lens. Then the "tear fluid" has to be a material with a refractive index $n_{tr}$ which is either larger or smaller than the lens index $n_1$, i.e. $n_{tr}>n_1$ or $n_{tr}<n_1$. With these adjustments in values for refractive indices, the described general dimensioning procedure applies also for lenses other than contact lenses.

For a lens in air according to the present invention, both $n_i$ and $n_{tr}$ have to be given the value 1. The general dimensioning procedure again applies also for lenses in air according to the present invention.

The steps can also be placed on the front surface of the lens. To one knowledgeable in the art, it is obvious how the general dimensioning procedure has to be adapted for the case where the steps are to be positioned on the front surface of the lens.

In practice, power profiles like the ones shown in FIGS. 2 and 4, respectively, will be approximated discontinuously by a certain number of discrete refractive powers. This approximation may be rather coarse, as demonstrated by the following example: FIG. 11 shows an approximation of power profile P1, and FIG. 12 shows the corresponding TFR of an assembly of lens zones which exhibit the power profile according to FIG. 11. A comparison between FIGS. 1 and 12 indicates that the approximation of the power profile P1 (FIG. 2) by the values given in FIG. 11 is valid. The TFR of FIG. 12 would apply for an intra-ocular lens with imaging properties both in distance (appr. 20 diopters) and near (approximately 24 diopters). This lens would also mask astigmatism due to its large depth of focus.

Power profiles of lens zones can also be designed such that the lens zones are multifocal. FIG. 13B shows, as an example, the TFR of a large depth of focus bifocal contact lens which comprises 9 lens zones on a diameter of 6.293 mm; all lens zones exhibit equal areas, i.e. the lens consists of Fresnel lens zones. In this example, the area of all lens zones is 3.46 mm² as depicted in FIG. 13A. The shape of the TFR of any of the lens zones (FIG. 13A) as well as the essentially identical shape of the TFR of the entire lens (FIG. 13B) is due to the power profile of the lens zones according to FIG. 14. It is interesting to note that the intensity associated with the effective lens power of 4 diopters (FIG. 13A and B) is very low, while half of the area of the lens zones exhibit the refractive power of 4 diopters (FIG. 14). This is another example of the fact that due to diffraction effects the resulting distribution of effective powers of a lens zone, which is characterized by the TFR, is different from the distribution of refractive powers (i.e., the power profile) given to this lens zone.

As is evident from the examples given in FIGS. 2, 4, 11 and 14, the power profile given to the lens zones determines the depth of focus and the shape of the TFR of the individual lens zone as well as the shape of the entire lens. Within these examples, the power profiles according to FIGS. 2 and 11 can be considered approximations of a combination of constant function, a half period of a sinusoidal function, and another constant function. The power profile according to FIG. 14 would be a coarse approximation of three quarters of a period of a sine function, and the power profile according to FIG. 4 represents a combination of an initial constant function and the approximation of a half period of a sinusoidal function consequently, the disclosed examples of useful power profiles can be considered approximations of a combination of at least one constant function and the fraction of a period of a sinusoidal function. Naturally, those skilled in the art will appreciate that the scope of useful power profiles is not restricted to this kind of approximations.

A circular lens or annular lens zone of 3.46 mm² area and single refractive power would exhibit a depth of focus of 1 diopter. The present lens comprising 9 lens zones of 3.46 mm² each has a depth of focus of 1.6 diopters in the lower power of 3 diopters and a depth of focus of 1 diopter in the higher power of 5 diopters. Consequently, the total depth of focus—which is manifest in two distinct powers—is 2.6 diopters, i.e. 2.6 times larger than the depth of focus of a lens zone of 3.46 mm² area and single refractive power.

Lens zones exhibit the same TFR if their areas are equal (Fresnel zones) and if they exhibit the same power profile. Consequently, the performance of a depth of focus lens which is composed of Fresnel zones of identical power profile is practically independent of lens aperture or pupil size.

A lens according to this invention with a large depth of focus may also be composed of annular lens zones of unequal areas. Then the lens performance will depend on lens aperture or pupil size.

FIG. 15 show various TFRs for a lens which is composed of lens zones of increasing area from center to rim. In this example the outer bonding radius $r_n$ of the n-th lens zone is given by $$r_n = r_1 \times n^{0.6}$$

and, consequently, the area $a_n$ of the n-th zone assumes the value $$a_n = a_1 [n^{2 \times 0.6} - (n-1)^{2 \times 0.6}]$$

wherein $r_1$ and $a_1$ are the radius and the area of the first zone, respectively. (Fresnel zones would exhibit the exponent 0.5 instead of 0.6 in the above equations.) The area $a_1$ of the innermost lens zone is 3.46 mm². All lens zones of the lens according to FIG. 15 are given the refractive power profile according to FIG. 14.

As can be seen from FIG. 15, the TFR of this depth of focus lens is dependent on lens aperture or pupil size, in contrast to the above examples. The total depth of focus is distributed over two powers. For all lens apertures the sum of the depths of focus in the two powers is at least twice as large as the depth of focus of a lens zone of constant refractive power and 3.46 mm² area, which is the area of the smallest lens zone of the lens according to FIG. 15. As can be seen from FIG. 15, the minimum depth of focus in either the lower or the higher power of this lens is 1.2 diopters, which is 1.2 times the depth of focus of a lens zone of constant power and 3.46 mm² area.

The introduction of optical path length differences is of paramount importance for the desired lens performance. This is obvious from a comparison of the FIGS. 15 and 16: FIGS. 15 and 16, respectively, show the TFRs of lenses which consist of the same lens zones, but optical steps of 5 microns are introduced in one lens (lens of FIG. 15), whereas the transitions between adjacent lens zones are smooth in the other lens (lens of FIG. 16). Since in the lens according to FIG. 16 the contributions of the various lens zones do not add incoherently, diffraction effects between zones result in rather undesirable TFRs of this lens.

As will be understood, numerous other possibilities exist for the combination of lens zones with equal or unequal areas and equal or unequal refractive zone power profiles. FIG. 15 gives the results for just one example.

In summary it has been shown that a large depth of focus can be given a circular lens or an annular lens, if this circular lens or annular lens is imparted an appropriate refractive power profile. As particularly shown in FIG. 7, the depth of focus of a lens zone of given area could be almost tripled in comparison with a lens zone of same area and constant refractive power by imparting the lens zone an appropriate refractive power profile. It has been further shown that the depth of focus of a lens zone of constant refractive power can be achieved by a lens zone of approximately 2.7 times larger area, if the larger area lens zone is imparted an appropriate power profile. Furthermore, it was particularly shown that the depth of focus of a lens which is composed of annular zones of areas in excess of 3.08 mm² exhibit a depth of focus well in excess of 1 diopter, if the lens zones of this lens exhibit appropriate refractive power profiles instead of single refractive powers. While prior art lenses according to U.S. Pat. No. 5,982,543 require lens zones with a maximum area of 0.0056λ mm², i.e. 3.08 mm², for achieving a depth of focus of 1 diopter, the lens according to the present invention achieves this depth of focus of 1 diopter with lens zones of an area of almost 10 mm² (see FIG. 7).

Although the illustrative embodiments of the present invention have been described herein with reference to the accompanying drawings, it is to be understood that the invention is not limited to those precise embodiments, and that various other changes and modifications may be effected therein by one skilled in that art without departing from the scope of the invention.

What is claimed is:

1. A lens zone exhibiting a depth of focus comprising a refractive power profile configured such that said depth of focus is at least 1.1 diopters for light of 550 nm wavelength, and wherein the area of said lens zone is at least 3.14 mm².

2. A lens zone according to claim 1, wherein the refractive power profile is configured such that the intensities within the depth of focus are at least 50% of the peak intensity within the depth of focus.

3. A lens zone according to claim 1, wherein the refractive power profile is configured such that the lens zone is a multifocal lens zone with at least two powers and wherein at least one of the powers exhibits said depth of focus.

4. A lens zone according to claim 1, wherein said lens zone is an annular lens.

5. A lens zone according to claim 1, wherein said lens zone is a circular lens.

6. A lens zone according to claim 1, wherein the power profile comprises an approximation of a combination of at least one constant function and a fraction of a period of a sinusoidal function.

7. A lens exhibiting a large depth of focus comprising:
at least two lens zones each lens zone having a refractive power profile wherein the depth of focus is at least 1.1 diopters for light of 550 nm wavelength and further wherein the area of each of said lens zones is at least 3.14 mm$^2$, and wherein optical path length differences are provided between adjacent lens zones such that light rays passing through adjacent lens zones have optical path lengths between an object point and an image point which are different by at least a coherence length of light, which is at least 1 μm.

8. A lens according to claim 7, wherein the refractive power profiles of the lens zones are identical.

9. A lens according to claim 7, wherein the refractive power profiles of the lens zones are different.

10. A lens according to claim 7, wherein the each of the lens zones exhibits refractive power profiles exhibiting at least two powers and wherein at least one of the powers exhibits said depth of focus.

11. A lens according to claim 7, wherein the areas of all of the lens zones are equal.

12. A lens according to claim 7, wherein the areas of all of the lens zones are different.

13. A lens according to claim 7, wherein the lens is an ophthalmic lens.

14. A lens according to claim 7, wherein the lens is a contact lens.

15. A lens according to claim 7, wherein the lens is an intra-ocular lens.

16. A lens exhibiting a depth of focus comprising:
at least two lens zones including a central circular lens zone and at least one annular lens zone surrounding the central circular lens zone, all lens zones configured such that light rays passing through adjacent lens zones have an optical path length between an object point and an image point which are different by at least a coherence length of light, passing through which is at least 1 μm, wherein the area of any of said lens zones is at least 3.14 mm$^2$ and wherein the lens zones are given refractive power profiles such that the depth of focus of any of the lens zones is at least 1.1 diopters for light of 550 nm wavelength.

17. A lens according to claim 16, wherein the refractive power profiles of all lens zones are equal.

18. A lens according to claim 16, wherein the refractive power profiles of each of the lens zones are different.

19. A lens according to claim 16, wherein the areas of all lens zones are equal.

20. A lens according to claim 16, wherein the areas of each of the lens zones are different.

21. A lens according to claim 16, wherein the shape of the through focus response of any of the lens zones is substantially identical with the shape of the through focus response of the entire lens.

22. A lens according to claim 16, wherein the lens is an ophthalmic lens.

23. A lens according to claim 16, wherein the lens is a contact lens.

24. A lens according to claim 16, wherein the lens is an intra-ocular lens.

25. A lens according to claim 16, wherein the lens is a intra-corneal lens.

* * * * *